United States Patent
Massoni

(10) Patent No.: US 7,435,269 B2
(45) Date of Patent: Oct. 14, 2008

(54) BISMUTH DYE SYSTEM FOR HUMAN HAIR

(75) Inventor: Jack Massoni, New Fairfield, CT (US)

(73) Assignee: Combe Incorporated, White Plains, NY (US)

( * ) Notice: Subject to any disclaimer, the term of this patent is extended or adjusted under 35 U.S.C. 154(b) by 305 days.

(21) Appl. No.: 11/266,858

(22) Filed: Nov. 4, 2005

(65) Prior Publication Data

US 2006/0096040 A1    May 11, 2006

Related U.S. Application Data

(60) Provisional application No. 60/625,616, filed on Nov. 5, 2004.

(51) Int. Cl.
 *A61Q 5/10* (2006.01)

(52) U.S. Cl. ............ 8/405; 8/406; 8/435; 8/587; 8/622

(58) Field of Classification Search ............ 8/405, 8/406, 435, 587, 622
See application file for complete search history.

(56) References Cited

U.S. PATENT DOCUMENTS 4,583,986 A * 4/1986 Lapidus ............ 8/405
5,972,237 A * 10/1999 Muller et al. ......... 252/186.39

* cited by examiner

*Primary Examiner*—Eisa B Elhilo
(74) *Attorney, Agent, or Firm*—James V. Costigan; Hedman & Costigan, P.C.

(57) ABSTRACT

A progressive hair dyeing composition which comprises the following ingredients:
(a) from 0.1 to 5 wt % of a bismuth salt;
(b) from 0.1 to 5 wt % of a thiosulfate compound;
(c) from 1 to 20 wt % of a delta-valerolactam;
(d) from 0.25 to 2.5 wt % of an alkaline agent;
(e) from 0 to 5 wt % of elemental sulfur; and
(f) from 50 to 90 wt % of water.

10 Claims, No Drawings

BISMUTH DYE SYSTEM FOR HUMAN HAIR

This Application claims the priority of provisional application Ser. No. 60/625,616, filed Nov. 5, 2004.

BACKGROUND OF THE INVENTION

Hair dye compositions for gradually coloring or darkening gray hair, usually referred to as progressive hair dyes, are well known in the art. Some of these compositions have been based on lead acetate. In order to avoid the use of lead in these products, bismuth salt based compositions have been described which have been considered as alternatives. The bismuth formulations have been considered to be inferior to the lead acetate formulations based on the quality of color they produce. These compositions included methyl pyrrolidone as a catalyst for fixing the bismuth salt to the hair shaft as a bismuth sulfide complex which is formed in situ by reaction of the bismuth salt with a thiosulfate. Compositions which contain methyl pyrrolidone are described in U.S. Pat. No. 4,583,986 which is incorporated by reference and other compositions of bismuth salt based hair dyes are disclosed in U.S. Pat. No. 4,310,329 which is also incorporated by reference.

Methyl pyrrolidone is under regulatory review in Europe and for this reason, this product is not desirable for long-term use as a component of a hair dye for human use. Accordingly, there is a need for an alternative catalyst for transforming a bismuth salt to a bismuth sulfide complex in the presence of a thiosulfate.

SUMMARY OF THE INVENTION

In accordance with the present invention, an aqueous dye composition is provided which comprises a bismuth salt, a thiosulfate and delta-valerolactam, as a catalyst. It has been found that delta-valerolactam produces a superior dyeing result as compared to the compositions which use methyl pyrrolidone.

Accordingly, it is a primary object of this invention to provide a novel catalyst for use in combination with a human hair dye comprised of a bismuth salt and thiosulfate.

It is also an object of this invention to provide an improved bismuth salt based dyeing composition which may be used to gradually color gray hair. These and other objects of the invention will become apparent from a review of the appended specification.

DETAILED DESCRIPTION OF THE INVENTION

The preferred dye compositions of the invention are formulated as follows:
(a) from 0.1 to 5 wt % of a bismuth salt;
(b) from 0.1 to 5 wt % of a thiosulfate compound;
(c) from 1 to 20 wt % of a delta-valerolactam;
(d) from 0.25 to 2.5 wt % of an alkaline agent;
(e) from 0 to 5 wt % of elemental sulfur; and
(f) from 50 to 90 wt % of water.

More preferred hair dye compositions according to the invention may comprise the following ingredients:
(a) from 0.5 to 2.0 wt % of a bismuth salt;
(b) from 0.5 to 2.0 wt % of a thiosulfate compound;
(c) from 5.0 to 10.0 wt % by weight of a delta-valerolactam;
(d) from 0.5 to 1.5 wt % of an alkaline agent; and
(e) from 75 to 90 wt % of water.

The bismuth salt may comprise bismuth citrate; bismuth carbonate, bismuth subsalicylate, bismuth nitrate; bismuth oxide; bismuth hydroxide; bismuth bromide; bismuth iodide; bismuth sulfate; and the like.

The thiosulfate may comprise a water soluble thiosulfate of an alkali metal such as sodium thiosulfate or potassium thiosulfate or the compound ammonium thiosulfate.

The alkaline agent is preferably an amine which is commonly employed as an alkalizing agent which will adjust the pH of the dye mixture to a pH of 6-10 and more preferably a pH in the range of 7.5-9. These alkalizing agents are those that are customarily used in hair dye compositions. Generally these materials comprise ammonium hydroxide, ammonia, compatible ammonia derivatives such as an alkylamine such as ethylamine, triethylamine, or alkanolamines such as monoethanolamine or triethanolamine or aminomethylpropanol; alkali metal carbonates, sodium hydroxide, potassium hydroxide and the like.

Delta-valerolactam or 2-piperidone is a known compound and is described in Chemical Abstracts.

Optional components of the hair dye composition may include a surfactant. The surfactants comprise well known materials and include polyethoxylated alcohols; polyethoxylated alkyl phenols; polyethoxylated organic ethers derived from fatty acids; polyethoxylated glyceryl esters and the like. Useful non-ionic surfactants are disclosed in U.S. Pat. No. 4,616,074 which is incorporated by reference. Preferred non-ionic surfactants include steareth-21 and polysorbate 80 as well as ethoxylated phenolic compounds. Examples of such compounds include octoxynol having 5-15 ethoxylated units per molecule which are commercially available as Triton X-100. Generally effective amounts of a surfactant are used which may vary from 0.01 to 1 wt %.

Because of its undesirable odor it may be desirable to avoid the use of elemental sulfur in certain compositions of the invention, but if desired, from 0.1 to 5 wt % of elemental sulfur may be included in the compositions of the invention.

Suitable fragrances and/or humecants and/or conditioners may also be added to the compositions of the invention as desired. Suitable humecants include di- or poly-hydroxy compounds such as glycerin or a liquid form of polyethylene glycol which may be used at a level of 20 to 70 wt %. If high levels of a humecant are used, the amount of water may be reduced.

The compositions of the invention may be made by dispersing the ingredients in water followed by the application of sufficient heat to dissolve the ingredients without causing decomposition. In the alternative, a suspension may be prepared when one or more of the ingredients are not soluble at the concentrations employed.

All weight percents are based on the total weight of the composition.

DESCRIPTION OF THE PREFERRED EMBODIMENTS

The following composition was prepared according to the present invention:

Example 1

| Ingredients | WT % |
| --- | --- |
| Bismuth Citrate | 0.500 |
| Triethanolamine | 0.900 |

-continued

| Ingredients | WT % |
|---|---|
| Sodium Thiosulfate | 1.000 |
| Fragrance | 0.200 |
| Octoxynol-9 | 0.100 |
| Delta-Valerolactam | 8.000 |
| D.I. Water | 89.300 |

The foregoing description of a preferred embodiment of the invention has been presented for purposes of illustration and description. It is not intended to be exhaustive or to limit the invention to the precise form disclosed. Obvious modifications or variations are possible in light of the above teachings. All such obvious modifications and variations are intended to be within the scope of the appended claims.

I claim:

1. A hair dyeing composition which comprises the following ingredients:
    (a) from 0.1 to 5 wt % of a bismuth salt;
    (b) from 0.1 to 5 wt % of a thiosulfate compound;
    (c) from 1 to 20 wt % of a delta-valerolactam;
    (d) from 0.25 to 2.5 wt % of an alkaline agent;
    (e) from 0 to 5 wt % of elemental sulfur and
    (f) from 50 to 90 wt % of water.

2. A hair dyeing composition as defined in claim 1 which also includes an alkaline material selected from the group consisting of ethanolamine and triethanolamine.

3. A hair dyeing composition as defined in claim 2 which includes a surfactant.

4. A hair dyeing composition as defined in claim 3 where the surfactant is selected from the group consisting of ethoxylated phenols.

5. A hair dyeing composition as defined in claim 3 which contains from 0.1 to 5 wt % of elemental sulfur.

6. A method of catalyzing a bismuth salt-thiosulfate containing hair dye, said method comprising adding to said hair dye an effective amount of delta-valerolactam.

7. A method of dyeing human gray hair, said method comprising applying a composition comprising:
    (a) from 0.1 to 5 wt % of a bismuth salt;
    (b) from 0.1 to 5 wt % of a thiosulfate compound;
    (c) from 1 to 20 wt % of a delta-valerolactam;
    (d) from 0.25 to 2.5 wt % of an alkaline agent;
    (e) from 0 to 5 wt % of elemental sulfur; and
    (f) from 50 to 90 wt % of water.

8. A method as defined in claim 6 where the composition also includes a surfactant.

9. A method as defined in claim 6 where the composition also includes from 0.1 to 5 wt % of elemental sulfur.

10. A hair dyeing composition which comprises the following ingredients:
    (a) from 0.1 to 5 wt % of a bismuth salt;
    (b) from 0.1 to 5 wt % of a thiosulfate compound;
    (c) from 1 to 20 wt % of a delta-valerolactam;
    (d) from 0.25 to 2.5 wt % of an alkaline agent;
    (e) from 0.1 to 5 wt % of elemental sulfur and
    (f) from 50 to 90 wt % of water.

* * * * *